United States Patent [19]

Harper et al.

[11] 4,338,464
[45] Jul. 6, 1982

[54] REMOVAL OF BROMOBUTANONE FROM ACETIC ACID

[75] Inventors: Jon J. Harper; Martin A. Zeitlin, both of Naperville, Ill.

[73] Assignee: Standard Oil Company (Indiana), Chicago, Ill.

[21] Appl. No.: 104,088

[22] Filed: Dec. 17, 1979

[51] Int. Cl.³ ............................................ C07C 51/43
[52] U.S. Cl. .................................................. 562/608
[58] Field of Search ....................... 562/608; 260/707; 62/541, 542, 532; 23/295 R

[56] References Cited

U.S. PATENT DOCUMENTS

| | | | |
|---|---|---|---|
| Re. 23,810 | 3/1954 | Schmidt | 260/707 |
| 2,823,242 | 2/1958 | McKay | 62/542 |
| 3,293,292 | 12/1966 | Oliver et al. | 562/549 |
| 3,561,225 | 2/1971 | Hinton | 62/542 |
| 4,111,986 | 9/1978 | Zimmerschied | 562/549 |

OTHER PUBLICATIONS

Arkenbout, CHEMTECH, 6, Sep. 1976, pp. 596-599 (1976).

Primary Examiner—Natalie Trousof
Assistant Examiner—James H. Reamer
Attorney, Agent, or Firm—Fred R. Ahlers; William T. McClain; William H. Magidson

[57] ABSTRACT

Acetic acid can be prepared in high conversions and selectively by the oxidation of liquid n-butane at temperatures of from 120° C. up to 230° C. in the presence of an acetic acid solution containing bromine ions in combination with ions of cobalt or cobalt and manganese. The debutanized effluent of such oxidation consists mainly of acetic acid and water but also contains esters and ketones boiling lower than acetic acid, some higher carbon content aliphatic acids and metal salts boiling higher than acetic acid and rather small amounts of 3-bromo-2-butanone which, although boiling higher than acetic acid, cannot be separated by simple distillation as can be the other non-acetic acid organic impurities. The present inventive technique for removal of said bromo-ketone has for its concept the use of a combination of cryogenic crystallization and removal of adhering mother liquor which can be practiced continuously in known apparatus devised for other fractional crystallizations.

6 Claims, No Drawings

REMOVAL OF BROMOBUTANONE FROM ACETIC ACID

FIELD OF INVENTION

This invention relates to removing a bromobutanone from otherwise impure acetic acid and more specifically pertains to decreasing the 3-bromo-2-butanone content of the fraction containing from 50 to 99 weight percent acetic acid obtained by removing unreacted butane from the effluent produced by the catalytic liquid phase oxidation of butane in the presence of catalysis provided by a combination of a source of bromine with one or more transition metal oxidation catalyst, more specifically cobalt, or manganese or cobalt and manganese.

STATE OF THE ART

According to U.S. Pat. No. 3,293,292 it is essential for the preparation of acetic acid to use both manganese and cobalt (e.g., in their 2+ form acetate tetrahydrates) with a source of bromine (e.g., ammonium bromide) to oxidize butane with oxygen gas in the liquid phase at 176°–177° C. and a gauge pressure of 65.4 kg/cm$^2$ in the presence of acetic acid as reaction solvent.

More recently U.S. Pat. No. 4,111,986 discloses that acetic acid can be prepared by contacting a sufficient concentration of oxygen-containing gas (e.g., oxygen gas at at least 5 liters per hour per 100 grams of butane) with normal liquid butane in the presence of an acetic acid solution of components of catalysis consisting essentially of cobalt (e.g., 1 to 50 milliequivalents per mole of butane) and bromine (2 to 500 milliequivalents per mole of butane). For this process, reaction temperatures of at least 176°–177° C. are preferred at gauge pressures of from 35 up to 211 kg/cm$^2$, preferably from 56 up to 105.5 kg/cm$^2$.

Concentrated acetic acid (even glacial) distilled from the effluent produced by the foregoing liquid phase oxidation processes is contaminated with bromine-containing compounds and is not generally suitable as an article of commerce even though the commercial specifications for glacial acetic acid or acetic anhydride do not set a maximum allowable value for bromine concentration.

Also acetic acid becomes contaminated with bromides when used as solvent or reaction medium for the liquid phase oxidation of alkyl-substituted aromatic compounds (e.g., xylenes, toluene, trimethyl benzenes) with air to the corresponding aromatic carboxylic acids in the presence of catalysis provided by the components comprising a combination of one or more transition metal oxidation metal catalyst and a source of bromine (e.g., Br$_2$, HBr, inorganic bromide salt, organic bromide (e.g., as tetrabromoethane). While some who practice such process for the production of aromatic carboxylic acids reuse the bromine-contaminated acetic acid in the oxidation process, others (e.g., the assignee of U.S. Pat. No. 3,578,706) prefer to remove the bromine or bromine-containing contaminants before reusing the acetic acid in the oxidation process.

According to said U.S. Pat. No. 3,578,706, the bromine-contaminated acetic acid is treated by reaction with a metal having electrochemical potential between manganese and iron, inclusive and then contacting the acetic acid through an anion exchanger to remove the bromine or bromides.

U.S. Pat. No. 2,884,451 is directed to removing odorous substances and materials of a reducing nature from acetic acid distilled from the product of non-catalytic oxidation of a C$_4$ to C$_8$ paraffinic hydrocarbon. The removal of said substances and materials is accomplished by catalytic hydrogenation of a liquid phase of said distilled acetic acid.

In our laboratories there has been under investigation the purification of acetic acid, including the removal of bromides therefrom, produced by the oxidation of a liquid phase of butane with oxygen in the presence of an acetic acid solution of a system of catalysis comprising the combination of bromine (e.g., bromine per se or inorganic or organic bromide) with one or more transition metal oxidation catalysts (e.g., Co or Co and Mn). While distillation and/or fractionation can remove most of the impurities including some of the inorganic bromine-containing impurities, the other bromine-containing compounds remain in the acetic acid product fraction at bromine concentrations of from 0.0005 weight percent up to 0.00015 weight percent. Such bromine contamination of the acetic acid fraction is not, we have also found, removed by catalytic (palladium metal disposed on activated carbon) hydrogenation of a liquid phase of the bromine-contaminated acetic acid fraction. Further, we found that such bromine contamination of the acetic acid fraction could not be suitably decreased by either contacting a liquid phase of said acetic acid fraction with an alkali metal hydroxide, bicarbonate or carbonate and then redistilling the acetic acid, or by contacting a liquid phase of said acetic acid with a solid absorbant.

However, it was discovered in our laboratories that the bromine content of said bromine-contaminated acetic acid fraction could be decreased to an acceptable low concentration by first contacting a vapor phase of said bromine-containing acetic acid fraction and hydrogen gas with a hydrogenation catalyst (e.g., metallic palladium or platinum or metallic palladium or platinum disposed on the surface of activated carbon and then either (1) contacting the vapors of so treated acetic acid with a bed of particles of solid absorbant (e.g., activated alumina or activated carbon or contacting a liquid phase of the hydrogenated acetic acid fraction with an alkali metal hydroxide, bicarbonate or carbonate and then redistilling the acetic acid. Said two- and three-step purification processes starting with catalytic vapor phase hydrogenation of the bromine-contaminated acetic acid fraction are, respectively, the subject of United States patent applications Ser. No. 970,226 and Ser. No. 970,222, both filed on Dec. 18, 1978. Both of those processes can decrease the bromine content of the acetic acid fraction below 3 weight parts of bromine per one million weight parts of acetic acid, the present lower limit of analytical routes for the determination of bromine.

We have now discovered that 3-bromo-2-butanone is the bromine source of contamination lingering in and difficult to remove from the acetic acid fraction and the bromine content contributor to the debutanized fraction of the fluid effluents obtained from butane oxidation in the presence of catalysis provided by bromine and either cobalt, or manganese, or cobalt and manganese as metal catalyst. We have also discovered that such bromine contamination can be substantially decreased by a simple cryogenic process.

STATEMENT OF THE INVENTION

According to the present invention the concentration of 3-bromo-2-butanone can be decreased in otherwise impure acetic acid by at least 70% by cooling such otherwise impure acetic acid to at least its freezing point temperature, separating solids frozen from the remaining acetic acid mother liquor, melting a minor portion of the separated solids, and washing the remaining solids with such melt. By such a combination of cryogenic (the freezing and melting temperatures are below 0° C.) fractional crystallization and wash steps, a substantial proportion of the 3-bromo-2-butanone remains in the acetic acid mother liquor and its acetic acid content decreases and appears in the washed product.

The "otherwise impure acetic acid" also containing 3-bromo-2-butanone used to remove said bromo-ketone by the present inventive cryogenic techniques is the debutanized portion of the liquid effluent obtained from the oxidation of liquid n-butane with oxygen gas at a temperature of from 120° C. up to 230° C. and a gauge pressure of from 50 up to 110 kg/cm$^2$ in the presence of acetic acid solution containing bromine ions in combination with ions of cobalt or cobalt and manganese to provide the system of catalytis. Such catalytic liquid phase oxidative prepartions of acetic acid from n-butane are disclosed in U.S. Pat. Nos. 4,111,986 and 3,293,292, respectively.

The present inventive combination of cryogenic crystallization and product washing is preferably conducted in a continuous manner in any one of several combinations of apparatus devised for such crystallization and wash steps.

The cooling step of the present process applied to the debutanized reaction effluent, which is mainly acetic acid (e.g., 66 to 72 weight percent) and water (25 to 20 weight percent), freezes out a different acetic acid-water (higher acetic acid content) eutectic mixture. Hence it is theoretically possible to isolate a substantially purified product through the use of only one crystallization step. But, since impurities are occluded in crystal imperfections or trapped as agglomerates, recrystallization is, as a practical matter, required to optimize purity. The acetic acid-water mixture to be purified appears not to form a solid solution upon freezing which for purification would need be accomplished in a multi-step operation. Continuous fractional crystallizations have been conducted commercially by employing one or more combinations of a scraped cold surface crystallization zone and a washing column.

Three systems for effective continuous crystallization are described by Gerard J. Arkenbout in CHEM-TECH, vol. 6, September, 1976, pages 596 to 599. Two of such systems comprise slow crystallization to maximize crystal purity and conveniently separable sized crystals followed by washing of the crystals formed by a melt of at least an outer portion of the last to form crystals in countercurrent flow with respect to crystal formation. One system effects such cooling and countercurrent washing by chilling the liquid feed in a long horizontal crystallizer whose inner surfaces, cooled by indirect heat exchange are scraped by a helical screw end which advances the crystals as they begin to form near the feed end through to the discharge end. The resulting suspension of crystals in mother liquor discharges into the upper portion of a vertical column having a reciprocating piston periodically pushing down from the top of the column past the entry of the slurry into the column and forcing the slurry downward and then withdrawing toward the top of the column. The column also has, at the upper portion thereof a wall filter which extends from just below entry of the suspension down to slightly below the furthest downward thrust of the piston. The compression of the entering suspension by the piston forces mother liquor through the wall filter and compacts the crystals against the downwardly moving bed of previously compressed crystals. Near the bottom portion of the column a heating zone is provided to melt the compacted crystals reaching said heating zone. A valved liquid product exit is provided in the bottom of the column. The flow of liquid through the valve is adjusted so that the downwardly moving bed of compacted crystals forces only a part of the melt of the crystals out of the bottom of the column which forces upwardly the remaining portion of the melt of the crystals. The upwardly forced portion of the melt of crystals flows past the next upward adjacent portion of crystals before they move into the melting zone and displaces mother liquor from and/or melts the outer surfaces of the next upward adjacent portion of crystals, thus forming a new liquid in contact with them of lower impurity content which continues upward displacement of mother liquor from and/or melting outer layers of crystals contacted. As the bed of compressed crystals moves downward in contact with the upwardly moving liquid, new crystals form or crystals grow which have a lower impurity content.

The second system containing the scraped wall surface chilling zone and vertical washing column has a long horizontal freezing zone made up of a series of chilled, scraped inner surface crystallization zones cooled by indirect heat exchange with a cold liquid. Each crystallization zone has not only scrapers to remove crystals from the cold inner surfaces but also has means for pumping least pure melt in the direction of the mother liquor discharge. The feed enters near the center of the last crystallization zone and the mother liquor is forced out one end of said zone. A temperature gradient is imposed on each of the crystallization zones such that a countercurrent flow of melt and crystals is established. Crystals formed in the coldest portion of the last crystallization zone are forced into the preceding zone and are first partially melted, the melt returning to the last crystallization zone and the unmelted crystals in contact with melt of purer crystals grow on the chilled surface and are forced further in the direction of the washing column. The crystals of increasing purity are forced into and downwardly through the column in contact with rising melt formed at the bottom of the column in its heated portion and rising through the column of the downwardly moving crystals and thence into the first section of the series of crystallization zones. In this system crystals are grown from a melt as pure as possible rather than from the least pure rejected waste.

In neither of the two foregoing systems does recrystallization contribute to product purification. Consequently the separation power of those two separation systems is rather limited.

The third system is a continuous purification accomplished not only by crystallization and countercurrent washing of crystals but also by repeated continuous recrystallizations accomplished in quite an unusual manner. The recrystallizations are not conducted by redissolving each crystal crop in an extraneous solvent. Rather the recrystallizations are accomplished by several steps of grinding crystals during their travel down through the wash column toward its bottom heating zone which melts the final crystals. Such grinding steps result in high separation efficiency per unit height of the wash column. The comminuting of the large crystals results in small particles which are not stable and dissolve in the upwardly moving surrounding liquid. The continuous comminuting of crystals and the travel of particles by countercurrent flow of melt liquor to a new pure liquid phase and recrystallization from such purer liquid phase ultimately results in the growth of larger purer crystals through the imposition of concentration differences, analogous to those of distillation or extraction.

Such grinding can be accomplished by a plurality of ball mills set at various levels in the wash column, for example, steel or ceramic balls on perforated trays or sieve discs with vibration of the balls and/or the trays or discs.

Such a system comprises a cooled and scraped surface crystallizer mounted in a vertical position at the top of a washing column having a plurality of perforated trays or sieve discs (e.g., 5 to 40 per meter of column height), a bottom heating zone to melt the last formed crystals washed with rising melt, a bottom discharge for liquid purified product, a feed inlet below the top, several (e.g., 2 to 4) trays or discs, and an upper outlet above the top disc or tray but below the crystallizer for discharge of impurity enriched liquor. An example of the number and size of the balls for the needed comminuting are 30 balls of 12 mm diameter per 80 mm diameter sieve disc having openings of 0.6×0.6 mm.

The temperatures suitable for fractional crystallization of the aqueous acetic acid compositions containing 3-bromo-2-butanone, according to this invention, are governed by their acetic acid-water contents which are the freezing temperatures thereof. Such freezing temperatures, for example, are known from tables of the freezing temperatures of acetic acid-water compositions and appear at pages 359 to 360 of vol. 4, the Physico-Chemical Constants of Binary Systems in Concentrated Solutions by Jean Timmermans, Interscience Publishers, Inc., New York 1960.

The following example is a simple batchwise attempt to decrease the 3-bromo-2-butanone content of the debutanized liquid reaction effluent from n-butane oxidation by the concept of the present invention.

EXAMPLE I

Impure acetic acid (hereafter "starting material"), comprises the debutanized liquid reaction effluent of the oxidation of liquid n-butane in the presence of cobalt and bromine ions at a temperature of 193° C. Such impure acetic acid is stirred and cooled to below −25° C. and held at that temperature for 5 minutes or less. The suspension of acetic acid-water crystals which are formed is separated by vacuum filtration at room temperature (20°–22° C.). The filter cake is removed, permitted to melt and the resulting liquid is collected. The composition of the starting material, filter cake liquid and mother liquor from analysis of the same are shown in TABLE I.

TABLE I
BATCHWISE CRYSTALLIZATION ACCORDING TO EXAMPLE I

| Component, Weight Percent | Starting Material | Filter Cake | Mother Liquor |
|---|---|---|---|
| Acetic Acid | 71.9 | 72.1 | 62.9 |
| 3-Bromo-2-Butanone | 1.03 | 0.79 | 1.24 |
| Propionic Acid | 1.03 | 0.79 | 1.32 |
| Butyric Acid | 0.466 | 0.376 | 0.596 |
| Acetone | 0.12 | 0.10 | 0.15 |
| Methyl Acetate | 1.98 | 1.45 | 2.04 |
| Ethyl Acetate | 1.41 | 1.05 | 1.57 |
| 2-Butanone | 1.99 | 1.48 | 2.35 |
| Sec-Butyl Acetate | 0.50 | 0.39 | 0.60 |
| n-Butyl Acetate | 0.04 | 0.03 | 0.05 |

The foregoing indicates, by the 23.3% decrease in 3-bromo-2-butanone concentration in the melt of the filter cake without washing adhering mother liquor from the filter cake, that suitable separation of 3-bromo-2-butanone can be accomplished by more efficient fractional crystallization which would include washing of the crystalline product.

In the simple purification technique of Example I the amount of mother liquor adhering to the crystals was in excess of that suitable for more complete removal of 3-bromo-2-butanone because its content is higher in the mother liquor than in the crystalline product. Such simple purification technique of Example I can be improved by the following modification.

EXAMPLE II

The cooling of the debutanized liquid effluent used in Example I is conducted to the same final temperature as in Example I. The suspension of crystals in mother liquor is transferred to a suction filter maintained at said final temperature so that the air drawn through the filter cake is at said final temperature. The filter cake is transferred to a second suction filter, and ambient air (about 20° to 21° C.) is drawn through the filter cake and warms it until liquid amounting to 8 to 15 weight percent of the filter cake drains therethrough. Thereafter the remaining filter cake is removed, permitted to melt and is collected as the final product. The 3-bromo-2-butanone content of the final product is substantially lower than that of the product of Example I, about 0.5 to 0.7 of the concentration in the product of said example.

Although washing the crystal cake with a partial melt thereof under batchwise conditions of Example II indicated that such a technique was somewhat effective for decreasing the content of 3-bromo-2-butanone in the impure acetic acid, such crystal washing conducted continuously in a countercurrent manner is more effective and can become even more effective when conducted in a manner which includes recrystallization.

EXAMPLE III

In this example the continuous fractional crystallization apparatus employed is a horizontal jacketed tube closed at one end and having its other end joined to the top of a vertical cylindrical column in fluid flow relationship. Said column has a closed bottom so that the combination of tube and column comprises a closed, fluid retaining system. Said horizontal tube having an inner helical ribbon screw driven at one end of the helical screw and pivotally supported at each end of the tube, to its discharge end and to scrape material frozen to the inner wall of the tube; a feed inlet 75 to 85% of the length of the tube away from its closed end and a waste liquid outlet near said closed end; and an inlet to the jacket around said tube near the closed end thereof and an outlet from said jacket near the junction of said tube and column; means for supplying a flow of chilled coolant to the inlet of the jacket, withdrawing warmed coolant from the outlet of the jacket and extracting heat by indirect heat exchange from the circulating coolant to chill it for its return to the jacket's inlet; a crystalline product melter near the bottom of the column; and a product discharge near the bottom closed end of the column. The helical ribbon screwscraper can be driven at a rate of from 0.5 up to 2 revolutions per minute.

The feed is debutanized fluid oxidation effluent from the oxidation of liquid butane with oxygen gas in an acetic acid solution containing cobalt and bromine ions conducted at a temperature of 193° C. Such debutanized fluid effluent is distilled to take as a single distillate the mixture hereafter designated "starting material" and leave a residue containing all the catalyst metal, the inorganic bromides and a small amount of the acetic acid. Said starting material at a temperature of 193° C. is fed to said apparatus. The coolant, a solution of water in ethylene glycol (about 40 wt.% water) at about −35° C. is fed to the jacket near the closed end of the horizontal tube. The ribbon screw-scraper is operated at about 1.0 rpm. The heater in the bottom of the washing column is operated to provide melt at a temperature between 16° C. up to 17° C. The temperature of the crystallizer at the feed inlet to the horizontal tube is between −20° C. and −30° C. The composition of the feed mixture ("starting material"), melted product and waste liquor are given in TABLE II to follow.

TABLE II
CONTINUOUS FRACTIONAL CRYSTALLIZATION

| Component, Weight Percent | Starting Material | Melted Product | Waste Liquor |
|---|---|---|---|
| Acetic Acid | 66.4 | 78.7 | 60.6 |
| 3-Bromo-2-Butanone | 0.72 | 0.06 | 0.77 |
| Propionic Acid | 1.12 | 0.49 | 1.26 |
| Butyric Acid | 0.22 | 0.05 | 0.27 |
| Acetone | 0.13 | 0.11 | 0.38 |
| Methyl Acetate | 1.95 | 0.66 | 2.11 |
| Ethyl Acetate | 1.75 | 0.41 | 1.79 |
| 2-Butanone | 2.20 | 0.78 | 2.45 |
| Sec-Butyl Acetate | 0.61 | — | 0.15 |
| n-Butyl Acetate | 0.05 | 0.005 | 0.095 |
| Water | 24.85 | 18.73 | 30.1 |

The invention claimed is:

1. The method of decreasing the 3-bromo-2-butanone content of the debutanized liquid effluent containing mainly acetic acid and water obtained from the catalytic oxidation of liquid n-butane with oxygen at a temperature of from 120° C. up to 230° C. and a gauge pressure of from 50 up to 110 kg/cm$^2$ in the presence of catalysis provided by a combination of the bromide ion with a cobalt ion or a mixture of cobalt and manganese ions; which method comprises subjecting said debutanized liquid effluent as feed to a combination of fractional crystallizations and washing to remove mother liquor adhering to the crystalline product wherein the feed enters a crystallization zone cooled to the freezing point temperature of the acetic acid-water composition of the debutanized liquid effluent feed thereby forming in addition to acetic acid-water crystals a waste liquor having a 3-bromo-2-butanone content higher than in said feed, separating the waste liquor from the crystals and removing any of it adhering to the crystals by warming the crystals to partially melt them and permitting the remaining crystals to contact such melt before being separated from the melt.

2. The method of claim 1 conducted continuously by introducing the debutanized liquid effluent as feed into a crystallization zone having a waste liquid outlet, a crystalline magma discharge attached to a washing zone, a feed inlet, and portions of said zone between said feed inlet and waste outlet cooled to decreasingly colder temperatures wherein the crystals formed are contacted in countercurrent flow with the liquid portion of the mother liquor as crystal precipitate therefrom as it flows from said inlet through the portions of said zone of decreasing temperature toward the waste outlet, the crystals leaving the mother liquor are contacted with a liquid comprising a partial melt of preceding crystals as they advance toward the product discharge in the washing zone, melting the product before it flows out of the product discharge, and permitting a portion of the product melt to flow countercurrent to and in contact with the advancing crystals so that the melt liquid composition in said flow increases in 3-bromo-2-butanone content as it advances to and mixes with the first formed mother liquor.

3. The method of claim 1 conducted continuously by introducing the debutanized liquid effluent as feed into a crystallization zone interconnected with a washing zone for series flow therethrough and having a temperature gradient imposed across the two zones such that the lowest temperature is at the point at which the waste liquor is discharged from the crystallization zone and the highest temperature is at the point where the product is discharged from the washing zone.

4. The method of claim 1 conducted by introducing debutanized liquid effluent as feed into a system comprising a crystallization zone having a feed inlet, a crystal slurry outlet and means for imposing a temperature gradient decreasing from said inlet to said slurry discharge, mechanically moving crystal slurry from its discharge past a filter to express mother liquor from the slurry through a filter and a waste liquor discharge and move the crystals into a washing zone joined in fluid flow relationship with the crystallization zone; said washing zone at its end opposite joining with the crystallization zone having a product outlet and means for melting crystals before the crystals reach the product outlet; wherein said washing zone at least a portion of the melt of crystals flows countercurrent to and through the crystal mass moving toward said melting means and forms a liquid of changing composition by causing crystal growth, increasing its 3-bromo-2-butanone content as it moves toward the filter, and removing mother liquor adhering to the crystals pressed past the filter; and wherein such liquid of changing composition mixes with the non-adhering mother liquor and the mixture is expressed through the filter.

5. The method of claim 1 conducted by continuously introducing the debutanized liquid effluent into the feed inlet of a system comprising a horizontal tubular crystallization zone closed at one end and cooled over substantially its entire length by indirect heat exchange and joined at its opposite end to the top of a vertical washing column closed at its bottom so that said combination defines a fluid retaining system; wherein said crystallization zone has a waste liquor discharge near the zone's closed end, the system's feed inlet is more than one-half the distance away from the waste liquor discharge and has means for removing crystals from the cooled inner wall and for moving such removed as well as precipitated crystals toward the washing column; and said washing column has a product discharge and a means for melting crystals at the closed bottom of said column; maintaining in the crystallization zone a temperature differential across the length of the zone whereby the lowest temperature is near the waste discharge and the temperature increases therefrom up to the freezing point of the feed at its inlet; maintaining a temperature differential over the height of the column comprising the range of from the melting point of product crystals down to the freezing point of the feed; moving the total crystals formed in the crystallization zone through the liquid moving therein and countercurrent therethrough to discharge said crystals into the washing column for their movement through the liquid rising in column caused by the melting of the product crystals and withdrawing of liquid product in an amount less than the crystals melted.

6. The continuous process of claim 5 wherein the feed, the acetic acid-water composition, contains 73 up to 78 weight percent acetic acid, and from 22 up to 27 weight percent water, the temperature at the crystallizer's inlet is from −20° C. to −30° C. and waste outlet is from −20° C. to −30° C., and the temperature of the melted product is 16° C.

* * * * *